United States Patent
Ren et al.

(10) Patent No.: US 9,645,379 B2
(45) Date of Patent: May 9, 2017

(54) MAGNIFICATION IN OPHTHALMIC PROCEDURES AND ASSOCIATED DEVICES, SYSTEMS, AND METHODS

(71) Applicant: NOVARTIS AG, Basel (CH)

(72) Inventors: Hugang Ren, Lake Forest, CA (US); Lingfeng Yu, Lake Forest, CA (US)

(73) Assignee: Novartis AG, Basel (CH)

( * ) Notice: Subject to any disclaimer, the term of this patent is extended or adjusted under 35 U.S.C. 154(b) by 217 days.

(21) Appl. No.: 14/584,685

(22) Filed: Dec. 29, 2014

(65) Prior Publication Data
US 2016/0183779 A1     Jun. 30, 2016

(51) Int. Cl.
| A61B 3/10 | (2006.01) |
|---|---|
| G02B 21/22 | (2006.01) |
| A61B 19/00 | (2006.01) |
| A61B 3/00 | (2006.01) |
| A61B 3/13 | (2006.01) |

(52) U.S. Cl.
CPC ............ *G02B 21/22* (2013.01); *A61B 3/0058* (2013.01); *A61B 3/132* (2013.01); *A61B 19/5223* (2013.01)

(58) Field of Classification Search
CPC ... A61B 3/0025; A61B 3/0041; A61B 3/0058; A61B 3/125; A61B 3/13; A61B 3/14

USPC ......................................... 351/205, 206, 219
See application file for complete search history.

(56) References Cited

U.S. PATENT DOCUMENTS

| 2012/0050308 A1* | 3/2012 | Nakano | A61B 3/0025 345/592 |
|---|---|---|---|
| 2015/0173644 A1* | 6/2015 | Ren | A61B 5/066 600/424 |

* cited by examiner

*Primary Examiner* — Huy K Mai

(57) ABSTRACT

An ophthalmic visualization system can include an imaging device configured to acquire images of a surgical field; a computing device configured to determine an area of interest based on the images; and a display device in communication with the computing device and a surgical microscope, wherein the display device is configured to provide a graphical overlay onto at least a portion of a field of view of the surgical microscope, and wherein the graphical overlay includes a magnified image of the area of interest. A method of visualizing an ophthalmic procedure can include receiving images of a surgical field acquired by an imaging device; identifying an area of interest; generating a graphical overlay including a magnified image of the area of the interest; and outputting the graphical overlay to a display device such that the graphical overlay is positioned over a field of view of a surgical microscope.

25 Claims, 15 Drawing Sheets

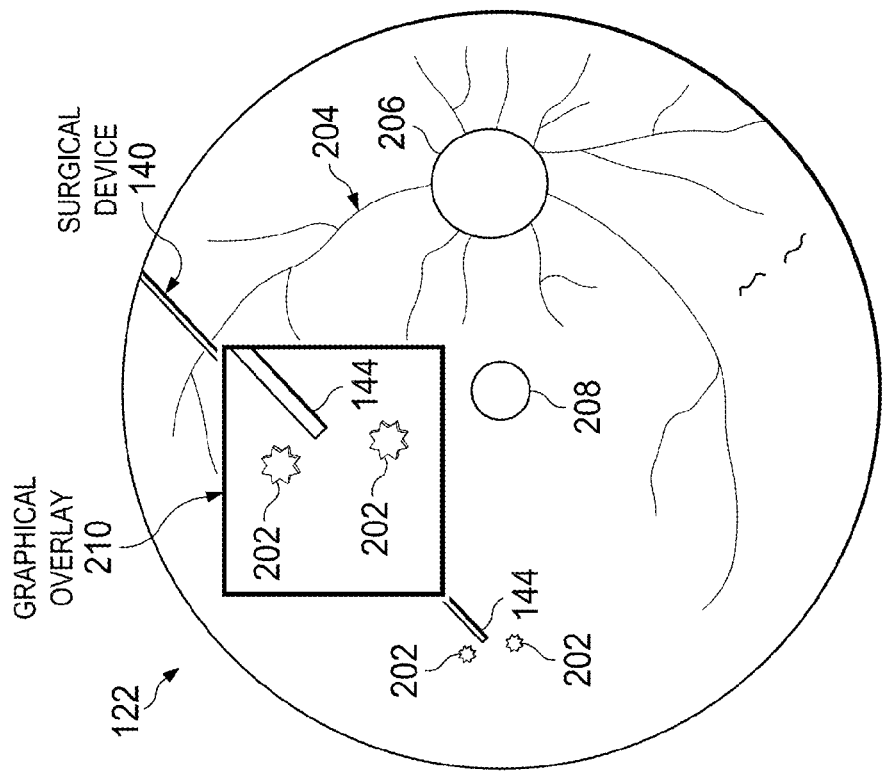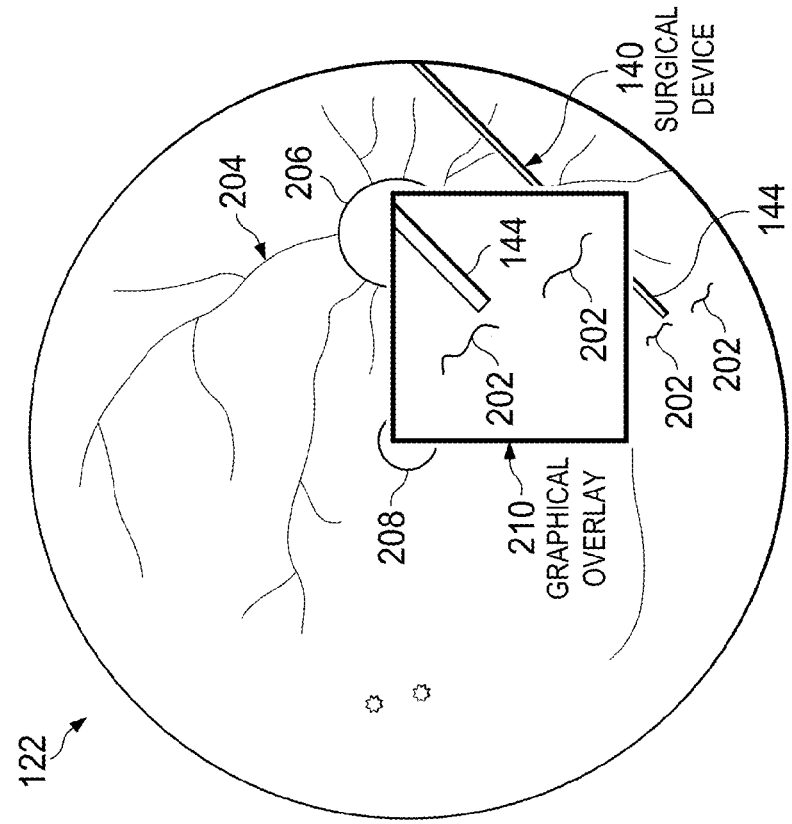

MAGNIFICATION IN OPHTHALMIC PROCEDURES AND ASSOCIATED DEVICES, SYSTEMS, AND METHODS

BACKGROUND

Technical Field

Embodiments disclosed herein relate to visualization in ophthalmic surgical systems. More specifically, embodiments described herein relate to displaying a magnified image of a surgical target area in the eye as a surgeon views the procedure using an optical surgical microscope, a digital microscope with an external display device, and/or other suitable displays.

Related Art

Ophthalmic microsurgical procedures can involve very small anatomy in the eye. Surgeons can perform the microsurgeries while observing the anatomy and surgical tools using a surgical microscope. Surgeons can have two conflicting preferences while visualizing the surgical procedure. First, high magnification can be preferred in order for the surgeon to visualize the fine structural details of biological tissue as well as to precisely control the surgical tools. Second, and at the same time, a large field of view can be preferred so that all the maneuvers during the surgical procedure occur within the same field of view for the surgeon and can help provide an overall context of the position of the tool(s) during the procedure.

Currently, the size of the objects, such as the biological tissue and the surgical tools, in the image viewed by the surgeon can be changed based on the zoom settings of the surgical microscope. With a high magnification, the object size can be large, but the field of view is small. With a low magnification, the field of view can be large, but the object size is small.

Accordingly, the surgeon can either choose an intermediate zoom for the surgical microscope to have an acceptable magnification with an acceptable field of view, or repeatedly change the zoom to obtain high magnification or large field of view one at a time as needed. With the former approach, the surgeon compromises visualization by not being able to resolve some fine details. With the latter approach, the surgeon needs to frequently adjust the microscope zoom, such as by physically pressing a foot pedal, while holding the surgical tool held steady within a patient's eye, which further complicates the procedure and can increase risk to the patient.

Accordingly, there remains a need for improved devices, systems, and methods that improve the ability to provide the surgeon high magnification images while simultaneously maintaining a large field of view by addressing one or more of the needs discussed above.

SUMMARY

The presented solution fills an unmet medical need with a unique solution to provide simultaneous high magnification and a large field of view while viewing a surgical procedure using a surgical microscope. An imaging device, such as a camera, can track the surgeon's area of interest, such as a tip of a surgical tool, in real time. The surgeon's area of interest can be magnified and overlaid onto a portion of the original field of view of the surgical microscope. The surgeon can view the magnified image as well as the original field of view. Thus, a large field of view and high magnification can be simultaneously obtained.

Consistent with some embodiments, an ophthalmic visualization system includes: a first imaging device configured to acquire first images of a surgical field; a computing device in communication with the first imaging device and configured to determine an area of interest in the surgical field based on the first images; and a first display device in communication with the computing device and a surgical microscope configured to image the surgical field, wherein the first display device is configured to provide a graphical overlay onto at least a portion of a field of view of the surgical microscope, and wherein the graphical overlay includes a magnified image of the area of interest.

Consistent with some embodiments, a method of visualizing an ophthalmic procedure includes: receiving first images of a surgical field acquired by a first imaging device; identifying an area of interest in the surgical field based on the first images; generating a graphical overlay including a magnified image of the area of the interest; and outputting the graphical overlay to a display device in communication with a surgical microscope configured to image the surgical field such that the graphical overlay is positioned over at least a portion of a field of view of the surgical microscope.

Additional aspects, features, and advantages of the present disclosure will become apparent from the following detailed description.

BRIEF DESCRIPTION OF THE DRAWINGS

FIGS. 2 and 3 are diagrammatic illustrations of views of a surgical field using an ophthalmic visualization system.

Figure 1:
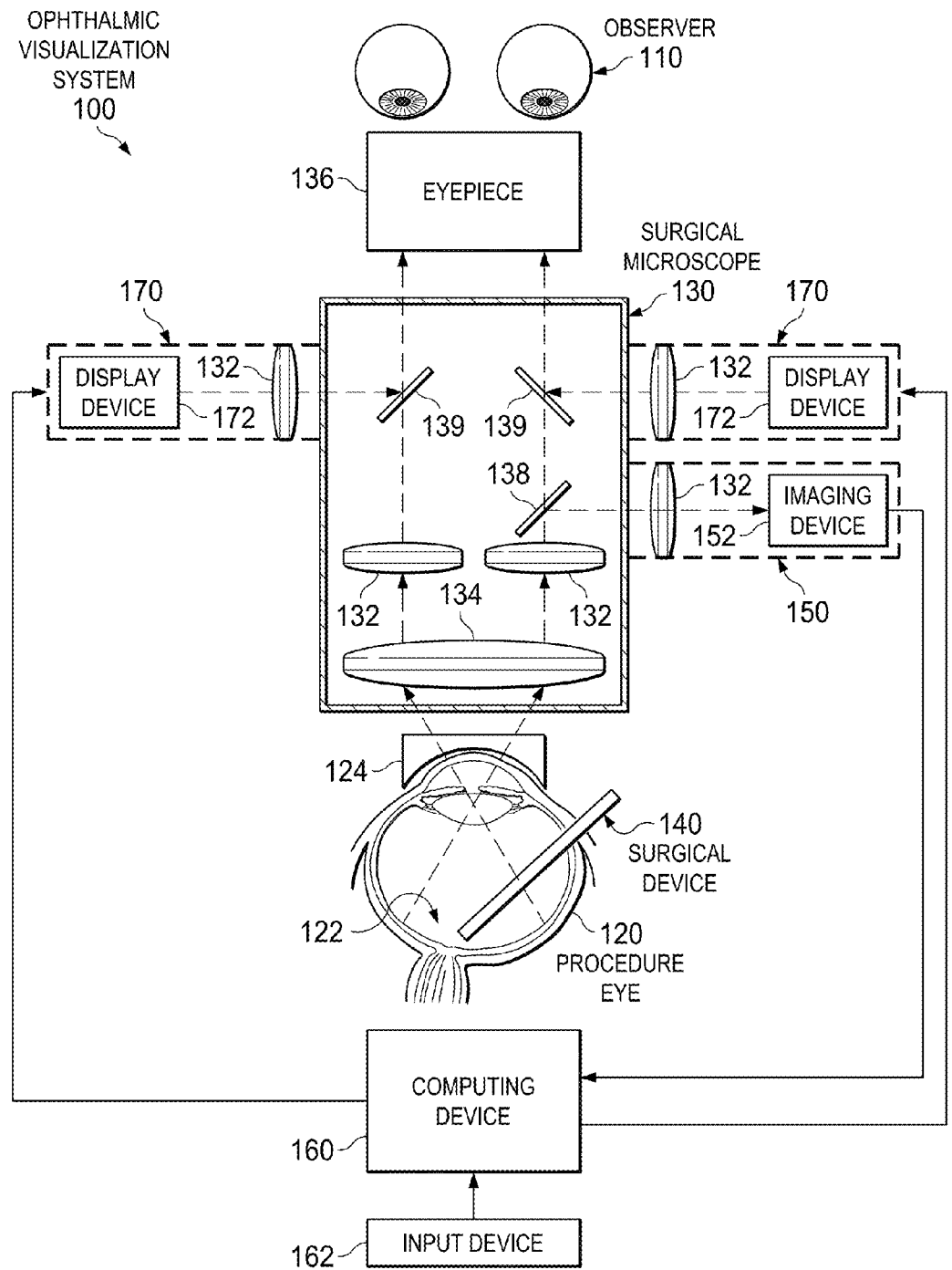
FIG. 1 is schematic diagram of an ophthalmic visualization system.

In the drawings, elements having the same designation have the same or similar functions.

DETAILED DESCRIPTION

In the following description specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art will realize other material that, although not specifically described herein, is within the scope and spirit of this disclosure.

The present disclosure describes devices, systems, and methods for simultaneously visualizing a large field of view and providing high magnification in an area of interest while a surgeon views a surgical procedure using a surgical microscope. An imaging device can acquire live, real time images of a surgical field that can include target biological tissue and a surgical device operating on the target biological tissue. A computing device can identify and track the surgeon's area of interest in the surgical field based on the images. For the example, the computing device can identify and track the tip of the surgical device. The computing device can also generate a graphical overlay including a magnified image of the area of the interest. The computing device can output the graphical overlay to a display device. The display device can provide the graphical overlay onto a portion of the original field of view of the surgical microscope. Thus, using the surgical microscope, the surgeon can view the surgical field and the graphical overlay simultaneously. The visualization system described herein can be described as a digital magnifying glass, in that it magnifies a region of interest without requiring attachment of an optical magnifying glass to a surgical tool or imaging component in a minimally invasive procedure.

The devices, systems, and methods of the present disclosure provide numerous advantages, including increasing surgical procedure efficiency and reducing risk of patient harm by eliminating the need to constantly change the surgical microscope zoom. The advantages of the present disclosure also include improving working conditions for the surgeon by (1) allowing a large field of view and high magnification simultaneously, and (2) permitting the graphical overlay to be transparent so that the portion of the original field of view over which the graphical overlay is positioned is visible using the surgical microscope. Devices, systems, and methods described herein also improve surgical procedure workflow by (3) allowing the graphical overlay to be selectively activated/deactivated; (4) allowing high magnification to be selectively provided; and (5) permitting magnification in minimally invasive surgeries when it is not possible to attach to attach a physical, optical magnifying glass to the surgical tool. Other advantages of the present disclosure include increasing implementation efficiency by (6) providing a low cost, universal approach for different surgical tools; (7) permitting use with current surgical tools without concerns about increasing tool size; and (8) providing flexibility with modular or surgical microscope-integrated approaches.

FIG. 1 illustrates an ophthalmic visualization system 100. The ophthalmic visualization system 100 can include an imaging device 152 configured to acquire images of a surgical field 122. The ophthalmic visualization system 100 can include a computing device 160 in communication with the imaging device 152 and configured to determine an area of interest in the surgical field 122 based on the images. The ophthalmic visualization system 100 can include a display device 172 in communication with the computing device 160 and a surgical microscope 130 configured to image the surgical field 122. The display device 172 can be configured to provide a graphical overlay onto at least a portion of a field of view of the surgical microscope. The graphical overlay can include a magnified image of the area of interest.

The observer 110, such as a surgeon or other medical professional, can visualize the surgical field 122 using the surgical microscope 130. During the surgical procedure, a surgical device 140 can be inserted into the procedure eye 120. In a vitrectomy procedure, for example, the surgical device 140 can be inserted into the vitreous chamber via an incision through the sclera in the pars plana. The surgical device 140 can be a cutting probe, a vitrectomy probe, laser probe, an ablation probe, a vacuum probe, a flushing probe, scissors, forceps, other suitable ophthalmic devices, and/or combinations thereof. Various other ophthalmic tools, such as a light source, an infusion cannula, etc., can also be inserted into the procedure eye 120 during the surgical procedure. The observer 110 can carry out the surgical procedure in the surgical field 122 using the surgical device 140. The surgical field 122 can include various biological tissue in the eye, including the vitreous humor, transparent membranes, portions of the retina, blood vessels, and/or other portions of the eye.

A contact lens 124 can be coupled to the procedure eye 120. The contact lens 124 can include one or more optical components, such as one or more suitable lens(es), configured to facilitate the view of the surgical field 122 for the observer 110. For example, the contact lens 124 can be a wide field of view lens. In another example, the contact lens 124 can be the GRIESHABER® DSP Aspheric Macular Lens available from Alcon, Inc. The contact lens 124 can also be configured to facilitate the surgical procedure, such as by fixating the procedure eye 120. For example, the contact lens 124 can be the LenSx® Laser SoftFit™ Patient Interface available from Alcon, Inc. The contact lens 124 can be coupled to and/or spaced from the surgical microscope 130. The contact lens 124 can be coupled to a stabilizing mechanism configured to stabilize the contact lens 124 relative to the procedure eye 120. To that end, the stabilizing mechanism can include one or more of a trocar, a counter weight, a friction-based system, and an elastic system. In some embodiments, a lens that is spaced from the procedure eye 120 is provided in the optical path between the procedure eye 120 and the surgical microscope 130. For example, a binocular indirect ophthalmomicroscope (BIOM) type or wide-field indirect contact lens can be used. The observer 110 can view the surgical field 122 through the contact lens 124, using the surgical microscope 130.

The surgical microscope 130 can be any suitable surgical microscope configured for use during an ophthalmic procedure. The surgical microscope can be an optical microscope and/or a digital microscope. In that regard, the surgical microscope 130 can include one or more lenses 132, such as focusing lens(es), zoom lens(es), and an objective lens 134, as well as mirrors, filters, gratings, and/or other optical components that comprise an optical train. The observer 110 can adjust the magnification and/or field of view by changing the relative positioning of the zoom lens(es). For example, the surgical microscope 130 can be in communication with a surgical footswitch that controls the zoom. An observer 110 can determine the preferred magnification at the beginning of the surgical procedure, such as one that provides a wide field of view of the surgical site. As described herein, a high magnification image of an area of interest in the surgical field 122 provided by the display device 172 can be viewed using the surgical microscope 130, without adjusting the magnification. Light reflected from the surgical field 122 can be received by the surgical microscope 130 and visualized by the observer 110, who views the surgical field 122 through the eyepiece 136. Exemplary views of the surgical field 122 using the ophthalmic visualization system 100 and the surgical microscope 130 are shown in FIGS. 2, 3, 6a-10b, and 14-16. When the surgical microscope 130 is a stereo microscope, as in the illustrated embodiment of FIG. 1, two optical paths (e.g., one for each eye of the observer 110) can be provided. Similarly, the eyepiece 136 can include separate oculars or other viewing components for each eye of the observer 110. The observer 110 can observe the field of view of the surgical microscope 130 and/or and the graphical overlay through the eyepiece 136.

As noted above, the ophthalmic visualization system 100 can include the imaging device 152. The imaging device 152 can be a digital imaging device. For example, a camera or video camera can be configured to acquire a series of still images or frames of the surgical field 122 that together form a live, real time view thereof. In that regard, the imaging device 152 can include an image sensor, such as a charge coupled device (CCD) image sensor, complementary metal-oxide-semiconductor (CMOS) sensor, and/or other suitable image sensors. The imaging device 152 can be configured to receive light reflected from the surgical field 122. The surgical microscope 130 can include a beam splitter 138 configured to guide a portion the reflected light to the imaging device 152 while allowing another portion of the reflected light to pass through to the eyepiece 136. The beam splitter 138 can include a glass prism, a metallic-coated mirror, a dichromic mirror, dichromic mirrored prism, a notch filter, a hot mirror, and/or a cold mirror. The portion of the reflected light directed towards the imaging device 152 can be split at any suitable point along the optical path, such as within or outside the surgical microscope 130. For example, the beam splitter 138 can be positioned between the eyepiece 136 and the zoom lens 132, as shown, or between the zoom lens 132 and the objective lens 134. The imaging device 152 can also include processing components, memory components, and/or other electrical components to interpret the light received at the image sensor and generate image data for use by the computing device 160 communicatively coupled thereto. The imaging device 152 can transmit the image data to the computing device 160.

The computing device 160 can include any suitable processing circuit, such as a processor communicatively coupled to a memory. The computing device 160 can be configured to perform the functions described herein. For example, the computing device 160 can receive and process the images acquired by the imaging device 152. The memory of the computing device 160 can store the pre-processed and/or post-processed image data. The computing device 160 can determine a surgeon's area of interest in the surgical field based on the images. The surgeon's area of interest can be determined in a variety of ways. For example, the computing device 160 can identify a portion of the surgical device 140, such as a marker, a distal portion, or a tip, disposed in the surgical field 122. Exemplary devices, systems, and methods for tool tracking are described in U.S. application Ser. No. 14/134,237, titled "Marker-Based Tool Tracking," and filed Dec. 19, 2013, the entirety of which is hereby incorporated by reference herein. Examples of tracking the surgical device 140 in the surgical field 122 are illustrated in FIGS. 6b, 7b, 8b, 9a-9d, and 14-16.

In another example, the observer 110 can identify the type of procedure or the target biological tissue for the computing device 160 via an input device 162. For example, the observer 110 can specify a macular surgery. The computing device 160 can be configured to automatically identify target biological tissue, such as by executing image recognition software that detects various tissue structures in the procedure eye 120 and compares them to known location, contours, and other anatomical features of the target biological tissue. In the example of macular surgery, the computing device 160 can determine the macula to be the area of interest and identify the macula and/or an area around the macula in the images received from the imaging device 152. Yet other methods of determining the surgeon's area of interest are contemplated.

The computing device 160 can generate display data representative of a graphical overlay. The graphical overlay can include a magnified image of the area of the interest. For example, the computing device 160 can perform a digital zoom on the images acquired by the imaging device 152 to increase the magnification in the area of interest. The computing device 160 can also enhance the image data, such as by modifying contrast, color tone, brightness, and/or other image parameters. The graphical overlay can provide a clearer view of the area of interest for the observer 110. The computing device 160 can transmit the display data representative of the graphical overlay to the display device 172 communicatively coupled thereto.

The graphical overlay can include images other than live images of the surgical field 122. For example, the computing device 160 can be configured to co-register the area of the interest determined based on the images acquired by the imaging device 152 with pre-acquired image(s) of the same anatomy. The pre-acquired images can include an optical coherence tomography (OCT) image, a fluorescein angiography image, an indocyanine green angiography image, a fundus photography image, a slitlamp biomicroscopy image, other suitable images, and/or combinations thereof. The computing device 160 can perform a digital zoom on the pre-acquired image. The computing device 160 can also enhance the pre-acquired image data, such as by modifying contrast, color tone, brightness, and/or other image parameters. The graphical overlay can include the magnified, pre-acquired image that shows the tissue corresponding to the determined area of interest. The computing device 160 can generate display data such that the portion of the pre-acquired image in the graphical overlay is updated as the real time area of interest changes. Providing both the live view and pre-acquired images of the area of interest can guide the surgeon during the surgical procedure, allow the surgeon to see the changes in the surgical field caused by the procedure, etc.

The display device 172 can be any suitable display device configured to provide a graphical overlay into the optical path of the surgical microscope 130. The display device 172 can be projection device, such as a digital light processing (DLP) device, a liquid crystal display (LCD) device, a light emitting diode (LED) device, a liquid crystal on silicon (LCoS) device, other suitable devices, and/or combinations thereof. The display device 172 can be in optical communication with the surgical microscope 130 such that the observer 110 can view the graphical overlay while simultaneously observing the surgical field 122 using the surgical microscope 130. The surgical microscope 130 can include a beam coupler 139 configured to combine the light from the display device 172 with the light reflected from the surgical field 122 such that the combined light is received at the eyepiece 136. The beam coupler 139 can include a glass prism, a metallic-coated mirror, a dichromic mirror, dichromic mirrored prism, a notch filter, a hot mirror, and/or a cold mirror. The light from the display device 172 can be combined with the reflected light at any suitable point along the optical path, such as within or outside the surgical microscope 130. The beam coupler 139 can be positioned between the eyepiece 136 and the objective lens 134, as shown.

The graphical overlay can be positioned over a portion of surgeon's field of view, as shown in FIGS. 2, 3, 6b, 7b, 8b, 9a-10b, and 16. The display device 172 can be configured to provide the graphical overlay with varying parameters, such as size, shape, position, transparency, etc., as described with respect to FIGS. 2, 3, 6b, 7b, 8b, and 9a-10b. With a stereo microscope, as in the illustrated embodiment of FIG. 1, one display device 170 can be provided for each of the two optical paths (e.g., one for each eye of the observer 110) or a single display device 170 can provide an output to each optical path.

As noted above, the ophthalmic visualization system 100 can also include the input device 162. The input device 162 can be in communication with the computing device 160. The input device 162 can be configured to allow the observer 110 to control ophthalmic visualization system 100, including activating/deactivating the graphical overlay, selecting whether the graphical overlay is provided in a fixed position or variable positions, selecting whether the graphical overlay is transparent or opaque, and/or other features described herein. The input device 162 may comprise any of a variety of ON/OFF switches, buttons, toggles, wheels, digital controls, touchscreen controls, or other user interface components. The input device 162 can integrally disposed on surgical microscope 130 and/or the surgical device 140. For example, the input device 162 can include one or more button(s) on a handheld portion of the surgical device 130 such that the graphical overlay can be selectively and instantaneously provided during the surgical procedure when the observer 110 depresses the button. The input device 162 can be a distinct component, such as, by way of non-limiting example, a surgical footswitch, a remote control device, a touchscreen control device, and/or another computing device. The ophthalmic visualization system 100 can include multiple input devices 162. The input device 162 can generate and transmit input signals based on the received user input. The computing device 160 can receive and process the input signal. The computing device 160 can generate and transmit control signals to the imaging device 152 and/or the display device 172 in response to the user input. The computing device 160 can also generate and provide the graphical overlay (e.g., in a fixed position, in varying positions, in a transparent or opaque manner, etc.) based on the received user input.

The imaging device 152, the display device 172, the computing device 160, and/or the input device 162 can be mechanically coupled to the surgical microscope 130. For example, the imaging device 152, the display device 172, the computing device 160, and/or the input device 162 can be integrated with or integrally disposed on/within the surgical microscope 130.

In another example, the imaging device 152, the display device 172, the computing device 160, and/or the input device 162 can be removably coupled to the surgical microscope 130. An example of a modular approach can be illustrated in FIG. 1. In that regard, the imaging device 152 can be part of a tracking and magnification module 150, and the display device 172 can be part of a projection module 170. The tracking and magnification module 150 and the projection module 170 can be removably coupled to surgical microscope 130. That is, a user (e.g., the observer 110, a surgeon, another physician, a nurse, a technician, etc.) can selectively add or remove one or more of the modules to selectively provide the features described herein. Thus, the imaging device 152, the display device 172, and/or other components described herein can be implemented in an existing surgical microscope by adding one or more modules. Accordingly, a hospital or other ophthalmic services provider can advantageously avoid the large capital expenditure associated with the acquisition of an entire surgical microscope that includes the imaging device 152, the display device 172, etc.

The surgical microscope 130, the tracking and magnification module 150, and the projection module 170 can include various components (e.g., wires, contacts, interfaces, the lenses 132, etc.) for facilitating electrical, optical, and/or data communication between the computing device 160, the imaging device 152, the display device 172, and/or the input device 162. Different combinations of components can be included in a given module. One or more of the imaging device(s) 152, the display device(s) 172, the input device(s) 162, and/or the computing device(s) 160 can be disposed in the same or different modules. One or more of the imaging device(s) 152, the display device(s) 172, the input device(s) 162, and/or the computing device 160(*s*) can be distinct from the surgical microscope 130 while one or more others of the components are mechanically coupled to the surgical microscope 130.

Figure 4:
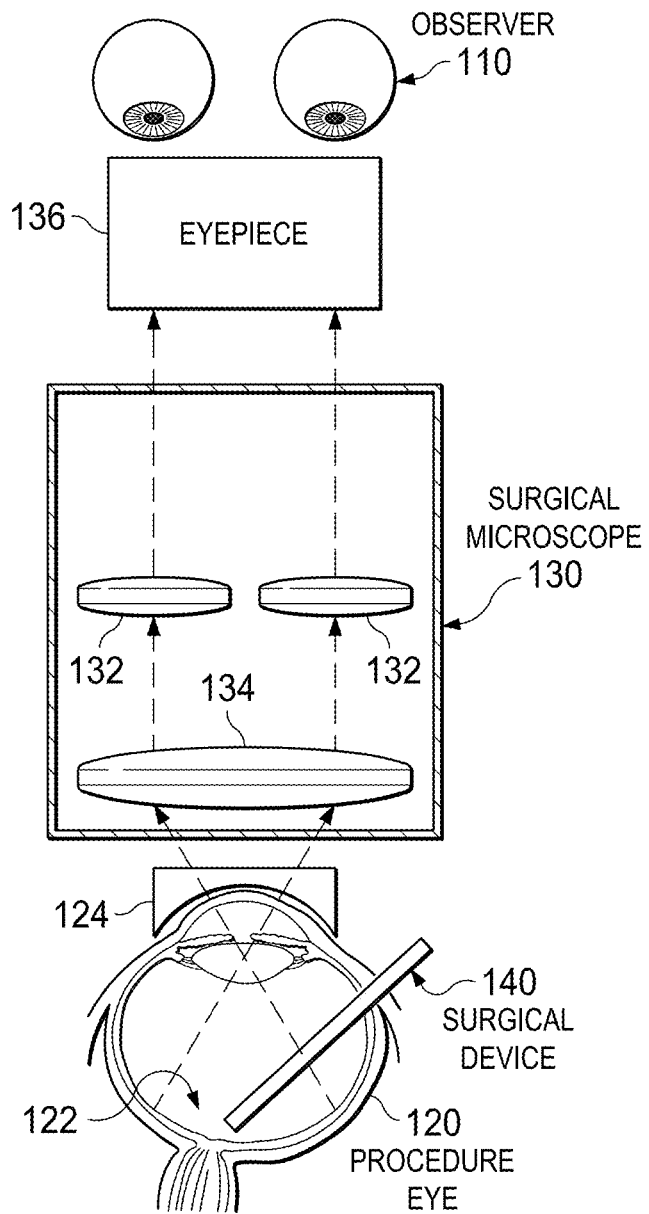
FIG. 4 is schematic diagram of a surgical microscope.
Figure 5:
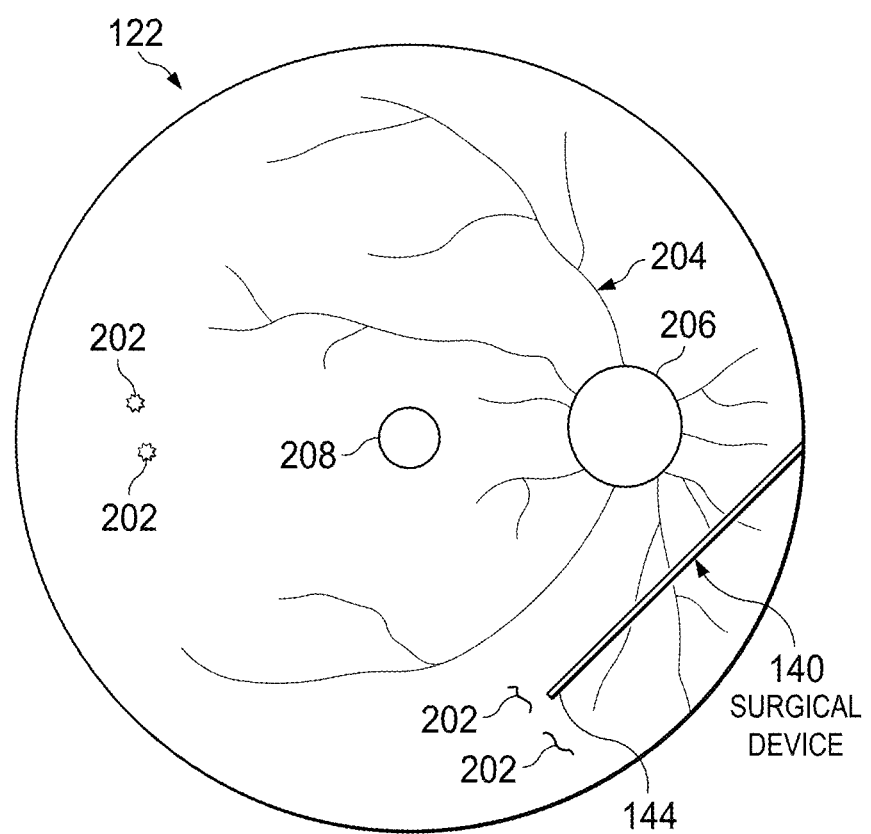
FIG. 5 is a diagrammatic illustration of a view of a surgical field using a surgical microscope.

FIGS. 2, 3, and 6*a*-10*b* illustrate views of the surgical field 122 using the ophthalmic visualization system 100. The surgical field 122 can include the surgical device 140, blood vessels 204, optic disk 206, macula 208, and fine features 202. The observer 110 can select the magnification of the surgical microscope 130 such that a field of view provides a desired perspective of the surgical field 122. FIGS. 2, 3, 6*b*, 7*b*, 8*b*, and 9*a*-10*b* show the graphical overlay 210 positioned over a portion of the surgical field 122. The graphical overlay 210 is shown to include a magnified image of the area of interest, which in the illustrated embodiment can be an area around the tip 144 of the surgical device 140. As shown for example in FIGS. 2 and 3, the graphical overlay 210 shows the fine features 202 and the tip 144 with increased size and clarity. The observer 110 can clearly visualize the fine features 202 with the graphical overlay 210 while simultaneously viewing the wide field of view of the surgical field 112. For comparison, FIG. 5 shows the surgical field 122 using the surgical microscope 130 of FIG. 4 without the graphical overlay 210. The same anatomy can be illustrated in FIG. 5 as FIGS. 2 and 3, but without the graphical overlay 210. A wide field of view is provided in FIG. 5, but neither the fine features 202 nor detailed position information about the tip 144 are readily visible by the surgeon.

Figure 6A:
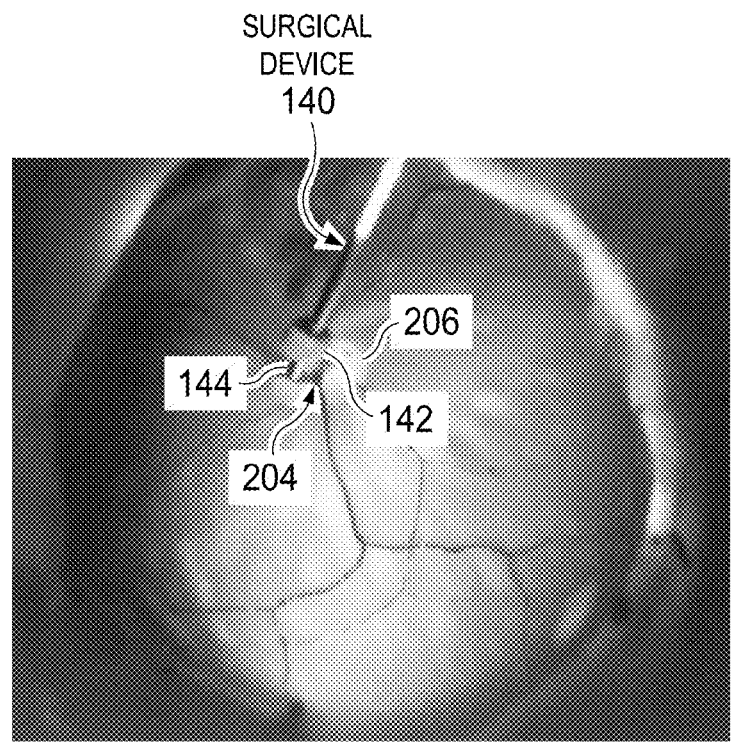
FIGS. 6a, 6b, 7a, 7b, 8a, 8b, 9a, 9b, 9c, 9d, 10a, and 10b are images of views of a surgical field using an ophthalmic visualization system.
Figure 6B:
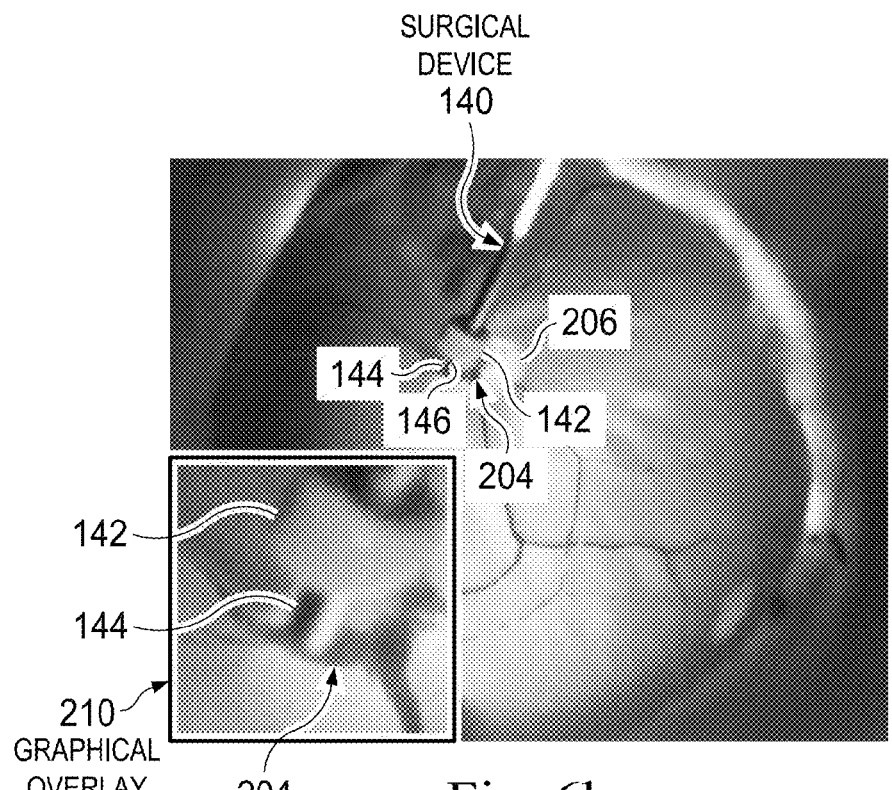
Figure 7A:
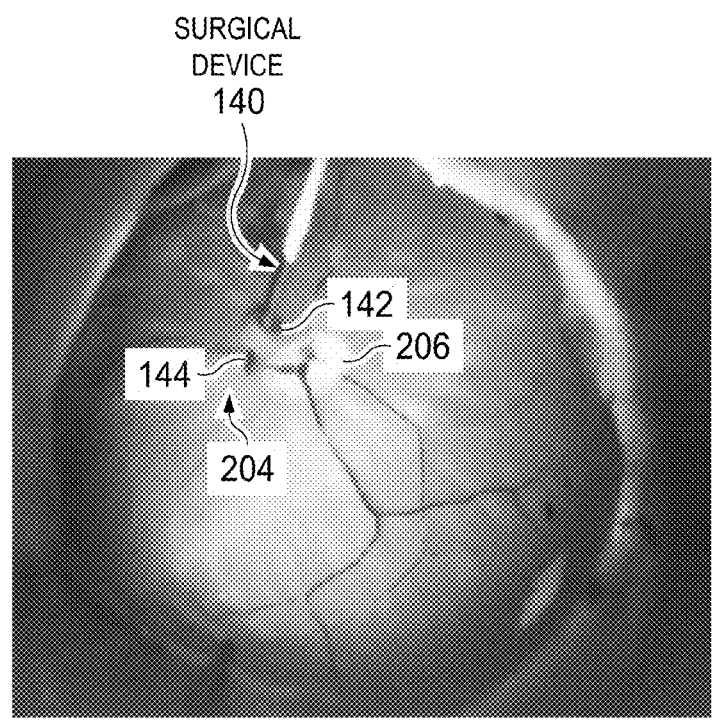
Figure 7B:
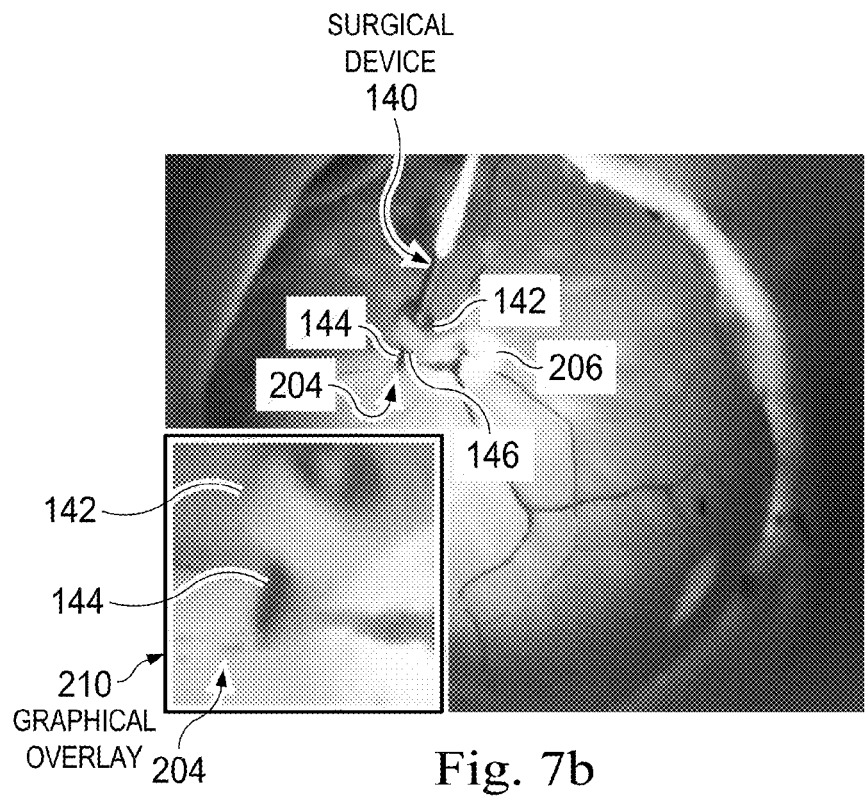
Figure 8A:
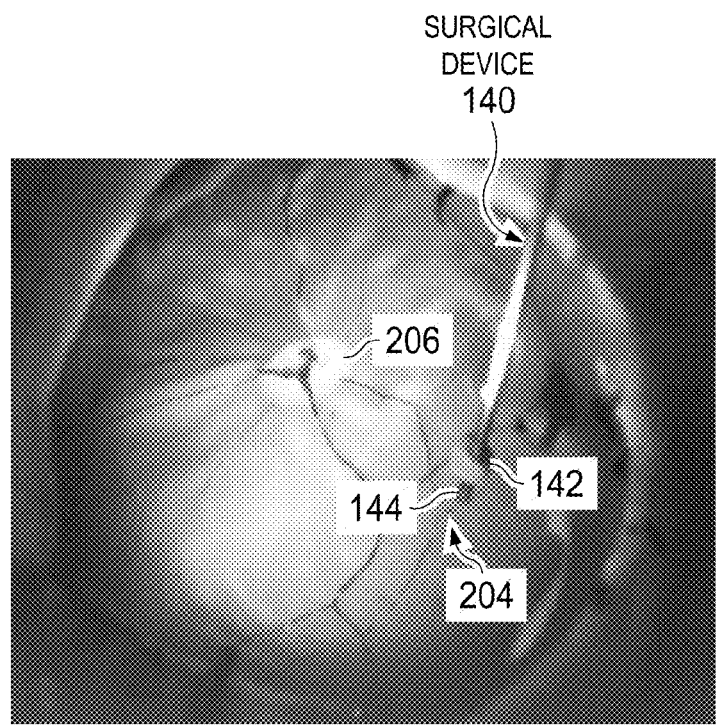
Figure 8B:
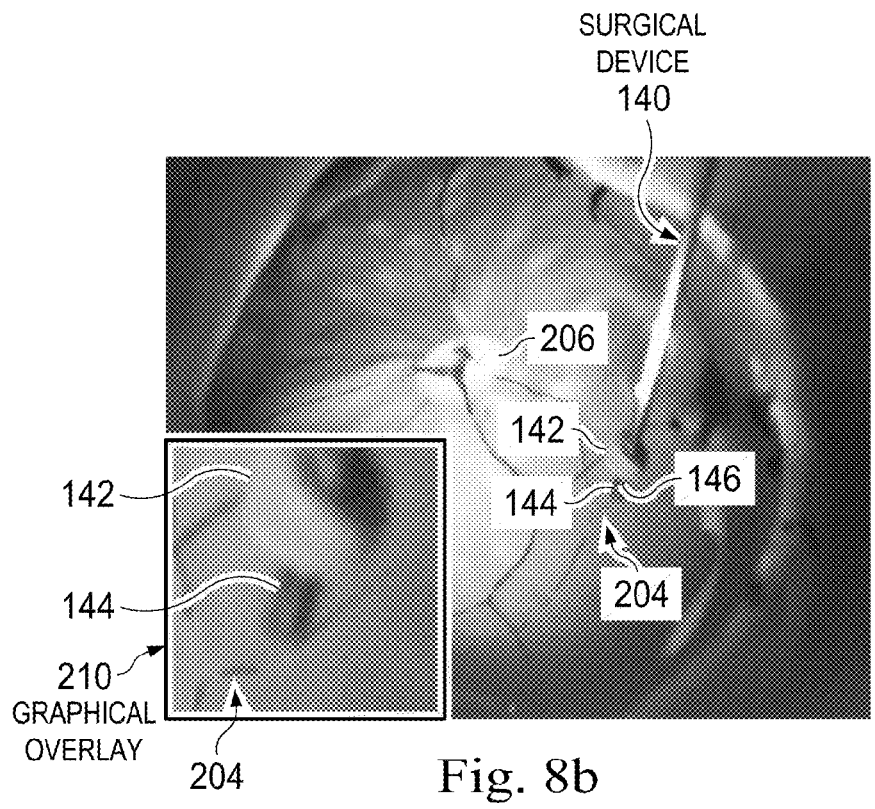
Figure 9A:
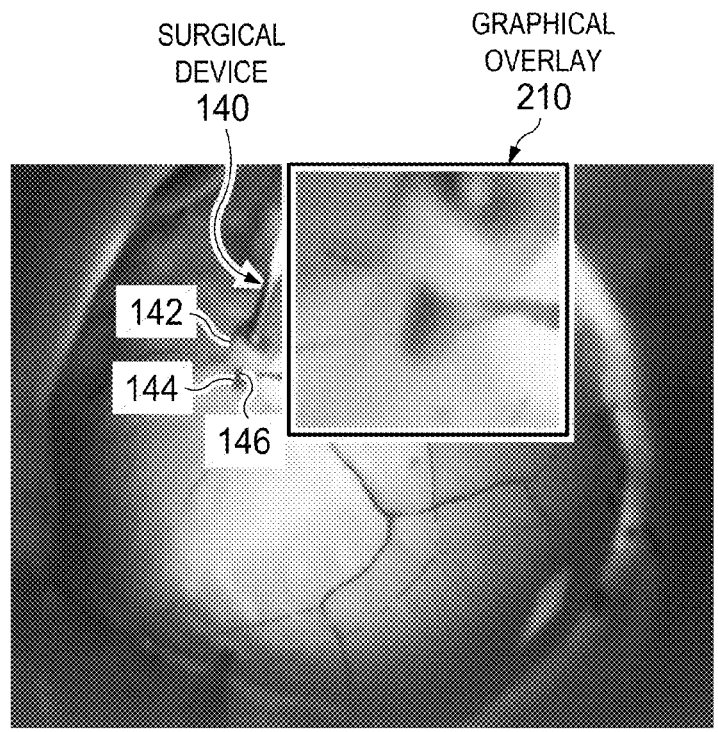
Figure 9B:
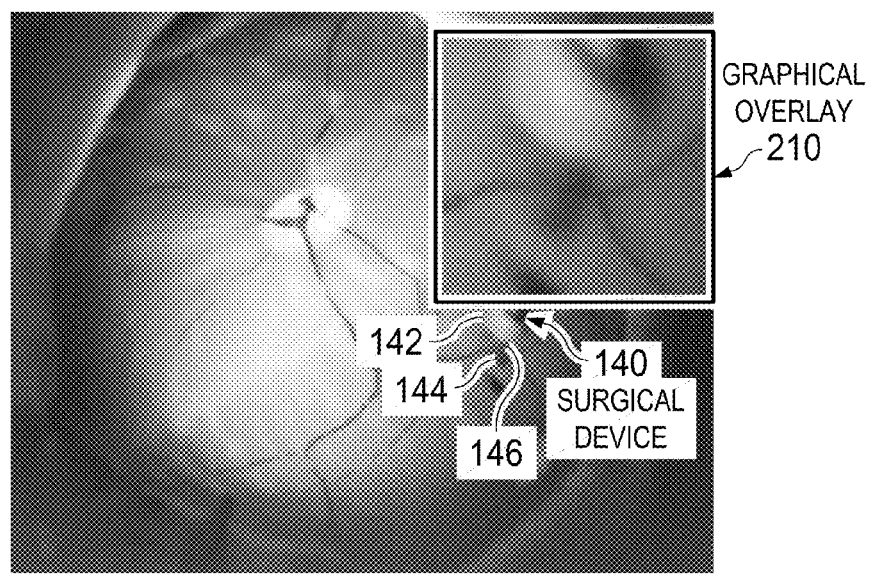
Figure 9C:
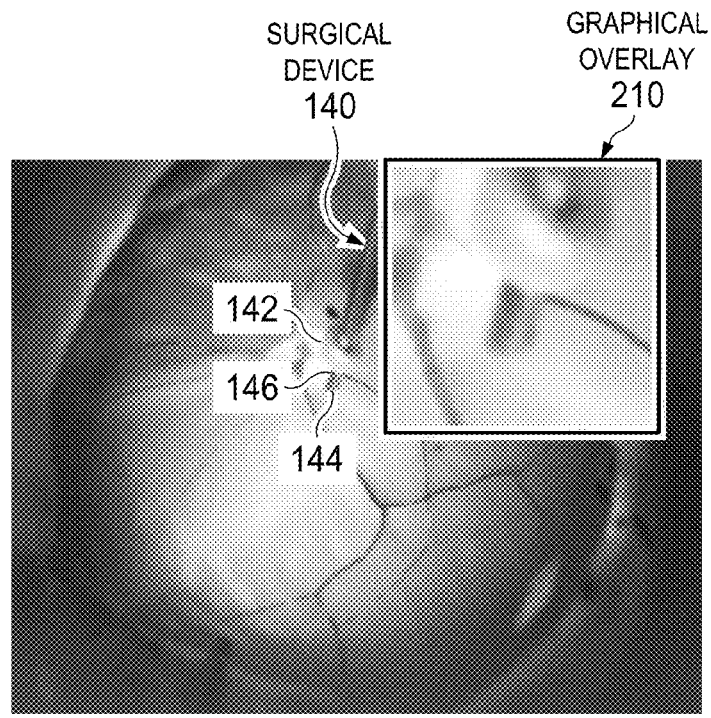
Figure 9D:
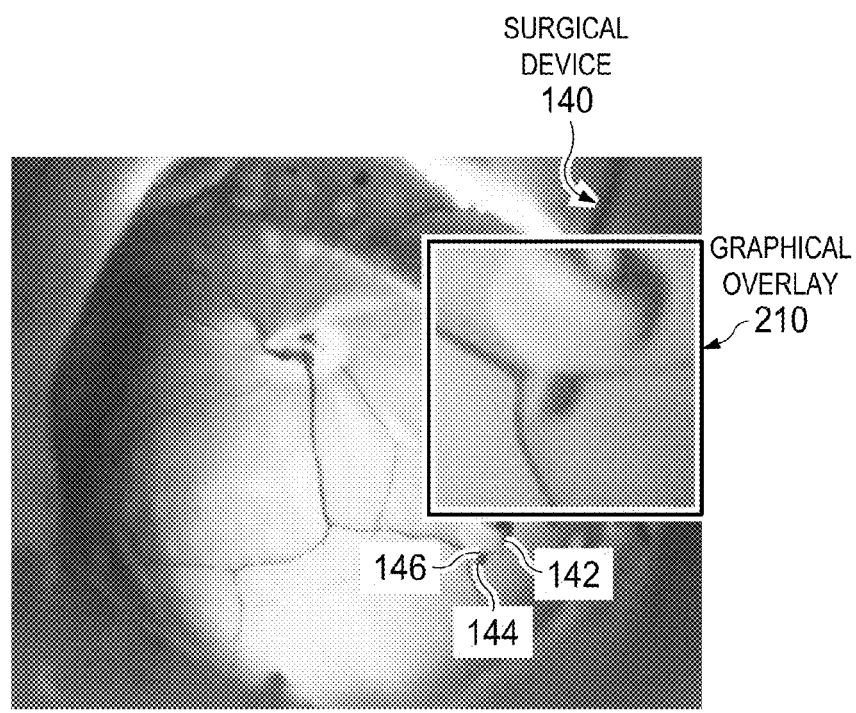

FIGS. 6*a*, 7*a*, and 8*a* illustrate views of the surgical field 122 using the ophthalmic visualization system 100, and FIGS. 6*b*, 7*b*, and 8*b* respectively illustrate the same anatomy with the graphical overlay 210. Comparing FIGS. 6*a*, 7*a*, and 8*a* with FIGS. 6*b*, 7*b*, and 8*b* can show the differences between the views of the observer 110 using the ophthalmic visualization system 100 with the graphical overlay 210 activated and deactivated. The surgical device 140 can include a marker 142 that can be identified and tracked by the computing device 160 in the images acquired by the imaging device 152. The display device 172 can be configured to provide an indicator 146 on the marker 142 on the wider field of view of the surgical field 122. The indicator 146 can alert the observer 110 that the tip 144 of the surgical device 140 is being tracked. The computing device 160 can be configured to generate associated display data.

A magnified image of the area of interest, such as the area around the tip 144, can be provided in the graphical overlay 210. Thus, details about the blood vessels 204 can be more clearly visualized. For example, in FIGS. 7*b* and 8*b*, the observer 110 can more clearly see discontinuities in the blood vessel 204, which are indicative of vessel segments that do not have red blood cells. Such fine details may not be easily visualized with the wider field of view alone, shown in FIGS. 7*a* and 8*a*, respectively.

The display device 172 can be configured to provide the graphical overlay 210 with any suitable size within the field of view of the surgical microscope 130. The computing device 160 can be configured to generate associated display data. For example, the graphical overlay 210 can occupy between about 5% and about 50%, between about 5% and about 40%, between about 10% and about 30%, between about 15% and about 25%, and/or other suitable proportions relative to the field of view of the observer 110 with the surgical microscope 130. In some embodiments, the observer 110 can select the size of the graphical overlay 210 via a user input using the input device 162. The observer 110 can modify the size during the surgical procedure. In some embodiments, the computing device 160 can automatically determine and/or modify the size of the graphical overlay 210. For example, the computing device 160 can be configured to determine that a surgical maneuver focuses on a relatively small area, such as when the marker 142 and/or the tip 144 has not moved a threshold distance within a threshold time. The computing device 160 can generate display data associated with a graphical overlay 210 that occupies a larger percentage of the field of view. The display device 172 can provide the larger graphical overlay 210 into the optical path of the surgical microscope 130. When the computing device 160 detects that a surgical maneuver spans a greater distance within the field of view, the size of the graphical overlay 210 can be decreased.

The display device 172 can be configured to provide the graphical overlay 210 with any shape within the field of view of the surgical microscope 130. The computing device 160 can be configured to generate associated display data. For example, the graphical overlay 210 can be a square, a rectangle, a polygon, a circle, an ellipse, other suitable shapes, and/or combinations thereof. The illustrated embodiments in FIGS. 2, 3, 6b, 7b, 8b, 9a-10b, and 16 show the graphical overlay 210 with a square shape. In some embodiments, an observer 110 can select the shape of the graphical overlay 210 via a user input using the input device 162. The observer 110 can modify the shape during the surgical procedure. In some embodiments, the computing device 160 can automatically determine and/or modify the shape of the graphical overlay 210. The graphical overlay 210 can include a border to distinguish the magnified image from the original field of the view of the surgical microscope 130. The observer 110 can selectively activate and deactivate the border, and/or change the visual characteristics of the border by providing a user input via the input device 162. The computing device 160 can be configured to generate associated display data.

The display device 172 can be configured to provide the graphical overlay 210 at any position within to the surgeon's field of view with the surgical microscope 130. For example, the graphical overlay 210 can be positioned at any corner, along the perimeter, spaced from the corners and/or the perimeter, and/or other suitable positions relative to the field of view. The illustrated embodiments in FIGS. 2 and 3 show that the graphical overlay 210 can be spaced from the perimeter of the field of view. The illustrated embodiments in FIGS. 6b, 7b, 8b, and 10 show that the graphical overlay 210 can be positioned at a corner of the field of view. The illustrated embodiments in FIGS. 9a-10b show that the graphical overlay 210 can be positioned along a perimeter of the field of view. The illustrated embodiments in FIGS. 9a-10b also show that the graphical overlay 210 can be positioned over a portion of the surgical device 140.

The display device 172 can be configured to provide the graphical overlay 210 at a fixed position. For example, the observer 110 can select the fixed position, such as the lower left corner or any other suitable position, via a user input using the input device 162. The computing device 160 can be configured to generate associated display data based on the input signal received from the input device 162.

The display device 172 can be configured to provide the graphical overlay 210 at different or variable positions relative to the surgeon's field of view with the surgical microscope 130. The observer 110 can select a position for the graphical overlay 210 at the beginning of the surgical procedure and modify the position during the surgical procedure, e.g., via a user input using the input device 162. The computing device 160 can be configured to generate associated display data based on the input signal received from the input device 162.

In some embodiments, the computing device 160 can automatically determine and/or modify the position of the graphical overlay 210 such that the position varies during the surgical procedure. The computing device 160 can be configured to identify and track the marker 142 and/or the tip 144 of the surgical device 140 in the images acquired by the imaging device 152 as the surgical device 140 moves in the surgical field 122. The computing device 160 can generate display data relating to the position of the graphical overlay 210 in response to the determined position of the marker 142 and/or the tip 144. The display device 172 can provide the graphical overlay 210 in the different positions such that the movement of the graphical overlay 210 corresponds to the movement of the marker 142 and/or the tip 144. For example, in FIGS. 9a-9d, the graphical overlay 210 is positioned proximate to, but spaced from, the marker 142 and/or the tip 144. The graphical overlay 210 can move with the surgical device 210. With such positioning, the graphical overlay 210 can cover a portion of the surgical device 140. This typically does not hinder the surgical procedure because the observer 110 uses the tip 144, which can remain un-obscured by the graphical overlay 210, to perform the procedure. The graphical overlay 210 can be positioned in an opposite position, relative to the marker 142 and/or the tip 144, within the field of view of surgical microscope 130. For example, if the computing device 160 determines that the marker 142 and/or the tip 144 is positioned in a lower right corner of the field of view, the graphical overlay 210 can be positioned in the upper left corner. The graphical overlay 210 can move to an opposite position as the tip 144 moves. The observer 110 select and/or switch between fixed and variable positions for the graphical overlay 210 via a user input using the input device 162. The computing device 160 can be configured to generate associated display data based on the input signal received from the input device 162.

Figure 10A:
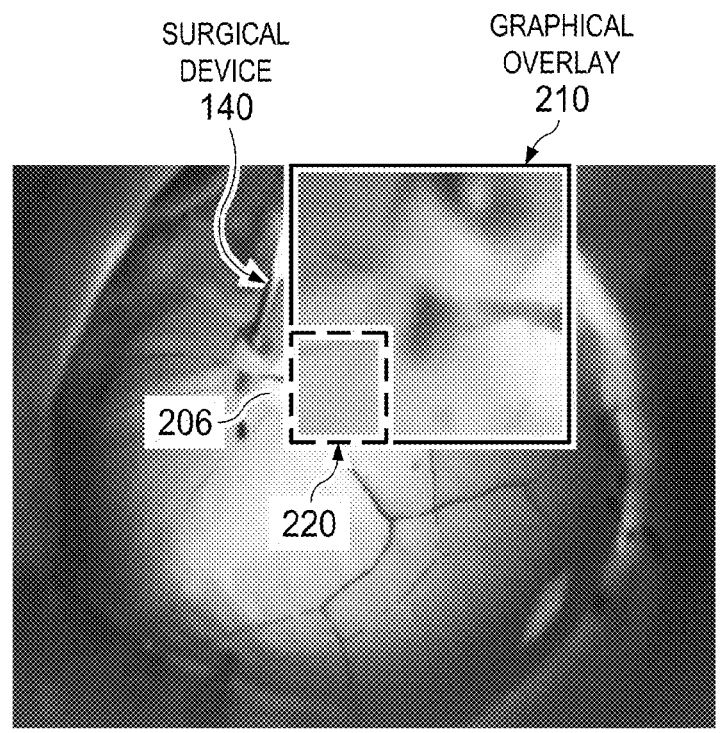
Figure 10B:
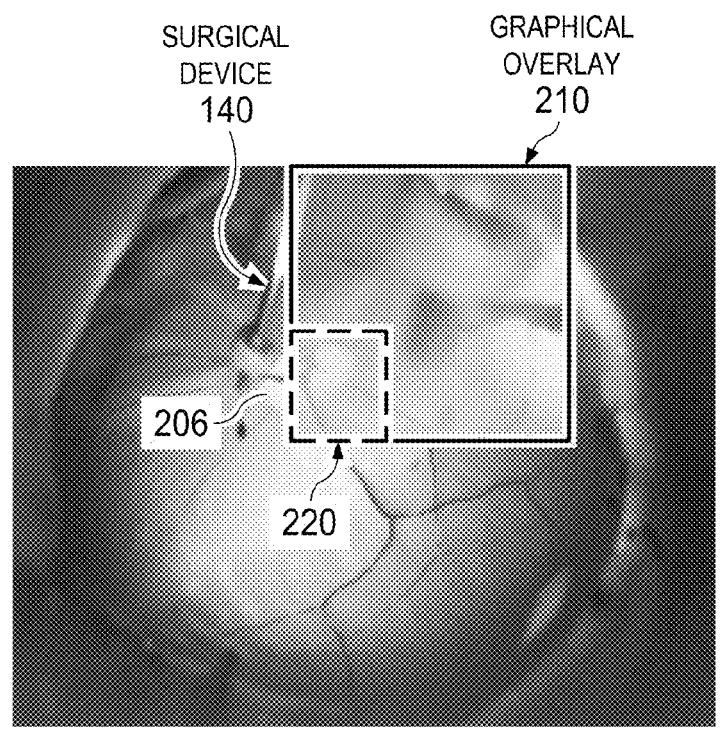

The display device 172 can be configured to provide the graphical overlay 210 in a transparent manner such that the surgical field 122 can be viewed through the graphical overlay 210. FIGS. 10a and 10b can illustrate the same anatomy with the graphical overlay 210 positioned over a portion of the optic disk 206. In FIG. 10a, the graphical overlay 210 can be opaque. The portion of the optic disk 206 can be obscured by the graphical overlay 210, as shown in region 220. In FIG. 10b, the graphical overlay 210 can be transparent. The portion of the optic disk 206 is visible through the graphical overlay 210, as shown in the region 220. In this manner, the entire surgical field 122 as well as the graphical overlay 210 can be simultaneously visualized using the surgical microscope. The observer 110 can activate/deactivate the transparency for the graphical overlay 210 via a user input using the input device 162. The observer 110 can also select a level for the transparency, such as between about 1% and about 99%, between about 10% and about 90%, between about 20% and about 80%, between about 30% and about 70%, and/or other suitable values. The computing device 160 can be configured to generate associated display data based on the input signal received from the input device 162. The display device 172 can be configured to provide the graphical overlay 210 in color while the background, wider field of view is provided in greyscale.

Such a configuration can provide additional contrast between the magnified image of the area of the interest in the graphical overlay 210 and the wider field of view with surgical microscope 130. The computing device 160 can be configured to generate associated display data.

Figure 11:
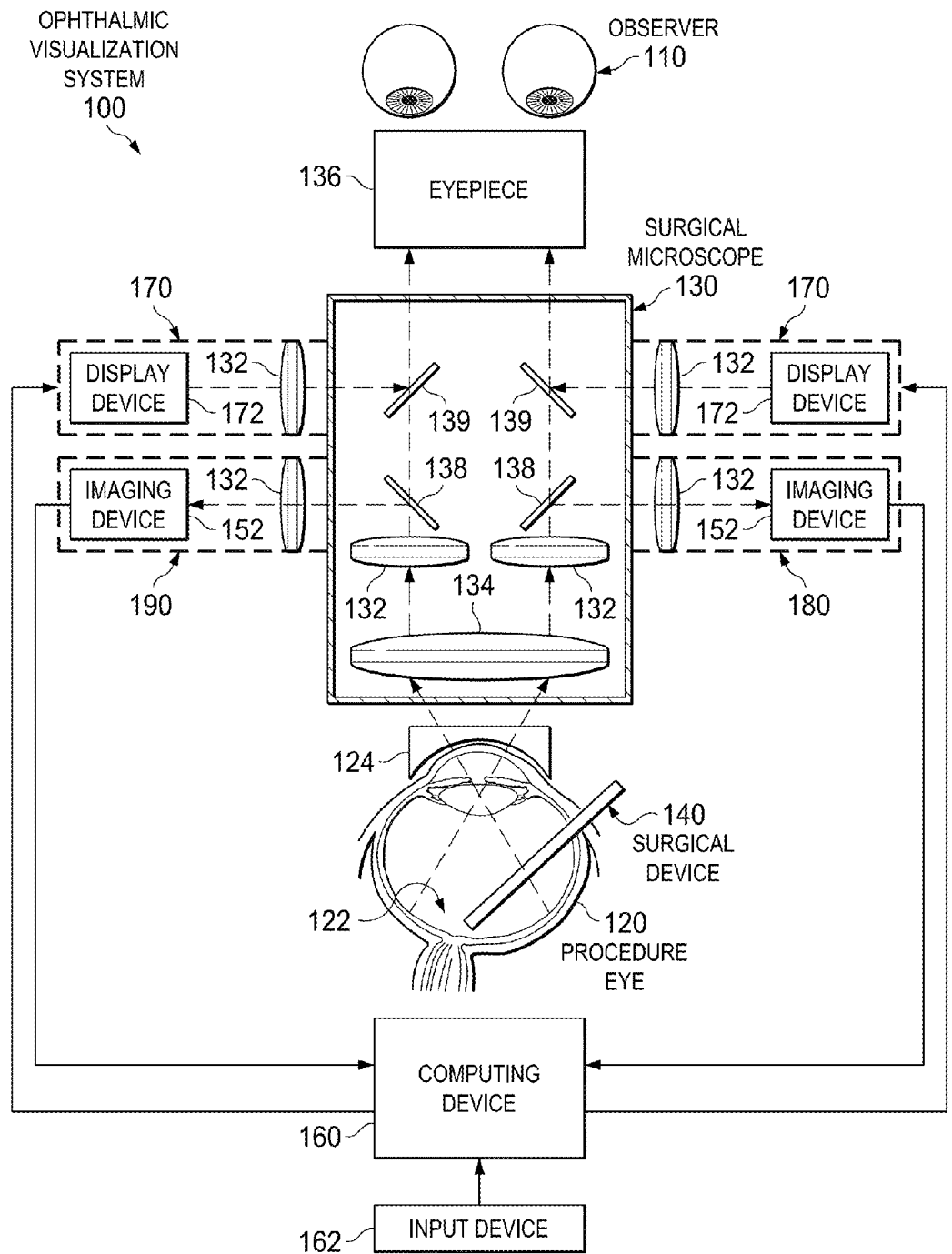
FIGS. 11, 12, and 13 are schematic diagrams of an ophthalmic visualization system.

FIG. 11 is a schematic diagram of the ophthalmic visualization system 100 that can include two imaging devices 152. Both of the imaging devices 152 can be configured to acquire images of the surgical field and transmit the images to the computing device 160. The quality of the images acquired by the two imaging devices 152 can differ. For example, one of the imaging devices 152 can be a standard resolution camera, while the other of the imaging devices 152 can be a high definition camera. The standard resolution camera can be configured to acquire relatively lower resolution images of the surgical field 122, while the high definition camera can be configured to acquire relatively higher resolution images. In another example, both of the imaging devices 152 can be the same or similar cameras, with one configured to acquire relatively lower resolution images and the other configured to acquire relatively higher resolution images. The computing device 160 can use the lower resolution images to identify the area of interest, such as the marker 142 and/or the tip 144 of the surgical device 140. Based on the identified area of interest in the lower resolution images, the computing device 160 can be configured to identify the corresponding location in the higher resolution images. The higher resolution images can be used to generate the graphical overlay 210. For example, the computing device 160 can perform a digital zoom on the high resolution image to generate a magnified image of the area of interest for the graphical overlay 210.

The efficiency of the ophthalmic visualization system 100 can be improved by decoupling tracking the area of interest from generating the graphical overlay 210. For example, one of the imaging devices 152 can be part of the tracking module 180 and the other of the imaging devices 152 can be part of the magnification module 190. The imaging device 152 can quickly transfer the lower resolution images to the computing device 160, which can quickly process the lower resolution images such that the area of interest is tracked in real time. Further, by performing the zooming in on the higher resolution images, the graphical overlay 210 can include even higher quality images of the area of interest, despite any decrease in resolution caused by the zoom.

Figure 12:
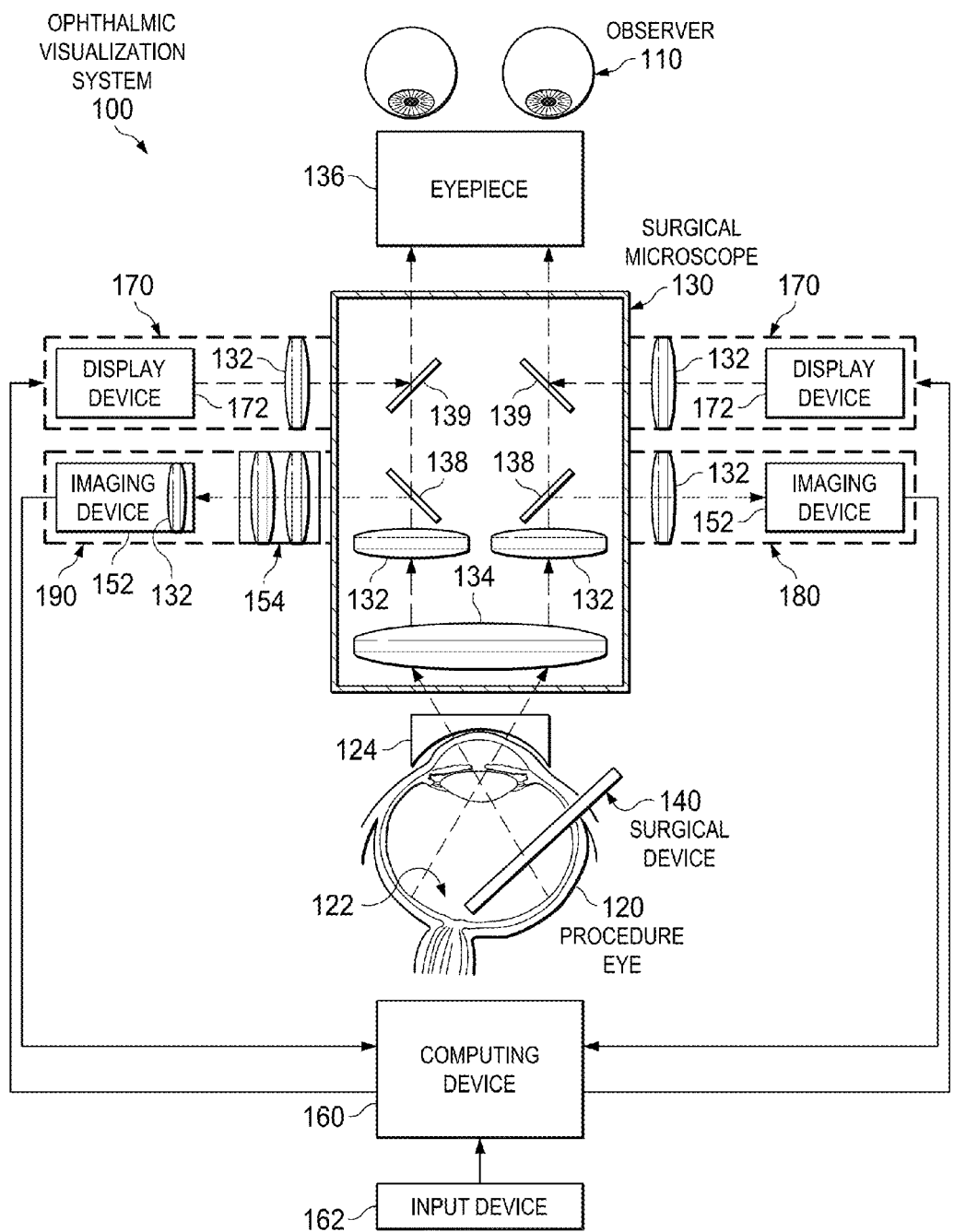

FIG. 12 is a schematic diagram of the ophthalmic visualization system 100 in which at least one of the imaging devices 152 can include optical zoom components 154. The optical zoom components 154 can include one or more lenses that can be moved relative to each other to adjust the magnification and/or field of view of the imaging device 152. The imaging device 152 and the optical zoom components 154 can be part of the magnification module 190. The magnification module 190 can also include other electrical, electromechanical, mechanical, and/or optical components to facilitate the features described herein. For example, the magnification module 190 can include various components (e.g., a suspension system, a mechanical frame, a protruding arm, a conical structure, a magnetic member, an elastic member, and a plastic member, etc.) configured to provide at least a portion of the imaging device 152 one or more rotational and/or translational degrees of freedom. Thus, the computing device 160 can actively control the field of view of the imaging device 152 by providing control signals to the components that move the imaging device 152 and/or adjust the optical zoom components 154. The optical zoom, position, and/or orientation of the imaging device 152 of the magnification module 190 can be modified such that the imaging device 152 is configured to acquire images of the area of interest. Optical zoom components 154 can be provided for both of the imaging devices 152.

During use of ophthalmic visualization system 100 of FIG. 12, the imaging device 152 of the tracking module 180 can acquire images of the surgical field 122. The computing device 160 can use the acquired images to identify the area of interest, such as the marker 142 and/or the tip 144 of the surgical device 140. Based on the identified area of interest in the acquired images, the computing device 160 can be configured to provide a control signal to the components in the magnification module 190 to adjust the optical zoom, position, and/or orientation of the imaging device 152 of the magnification module 190 to acquire images of the area of interest (as opposed to the entire surgical field 122). The imaging device 152 of the magnification module 190 can be movable and/or the optical zoom components 154 can be adjustable to track the area of interest as it changes position, such as when the tip 144 of surgical device 140 moves. The resulting images of the area of interest can be used to generate the graphical overlay 210. For example, the computing device 160 can use the images from the imaging device 152 of the magnification module 190 for the graphical overlay 210 without performing digital zoom because the acquired images are optically magnified and/or focused on the area of interest.

The quality of the images provided in the graphical overlay 210 of the ophthalmic visualization system 100 can be improved by including zoom components 154 as well as allowing active control of the position and/or orientation of the imaging device 152. By acquiring optically zoomed images of the area of interest, the images can be used for the graphical overlay 210 with higher resolution as compared to zooming in on a wider field of view image.

Figure 13:
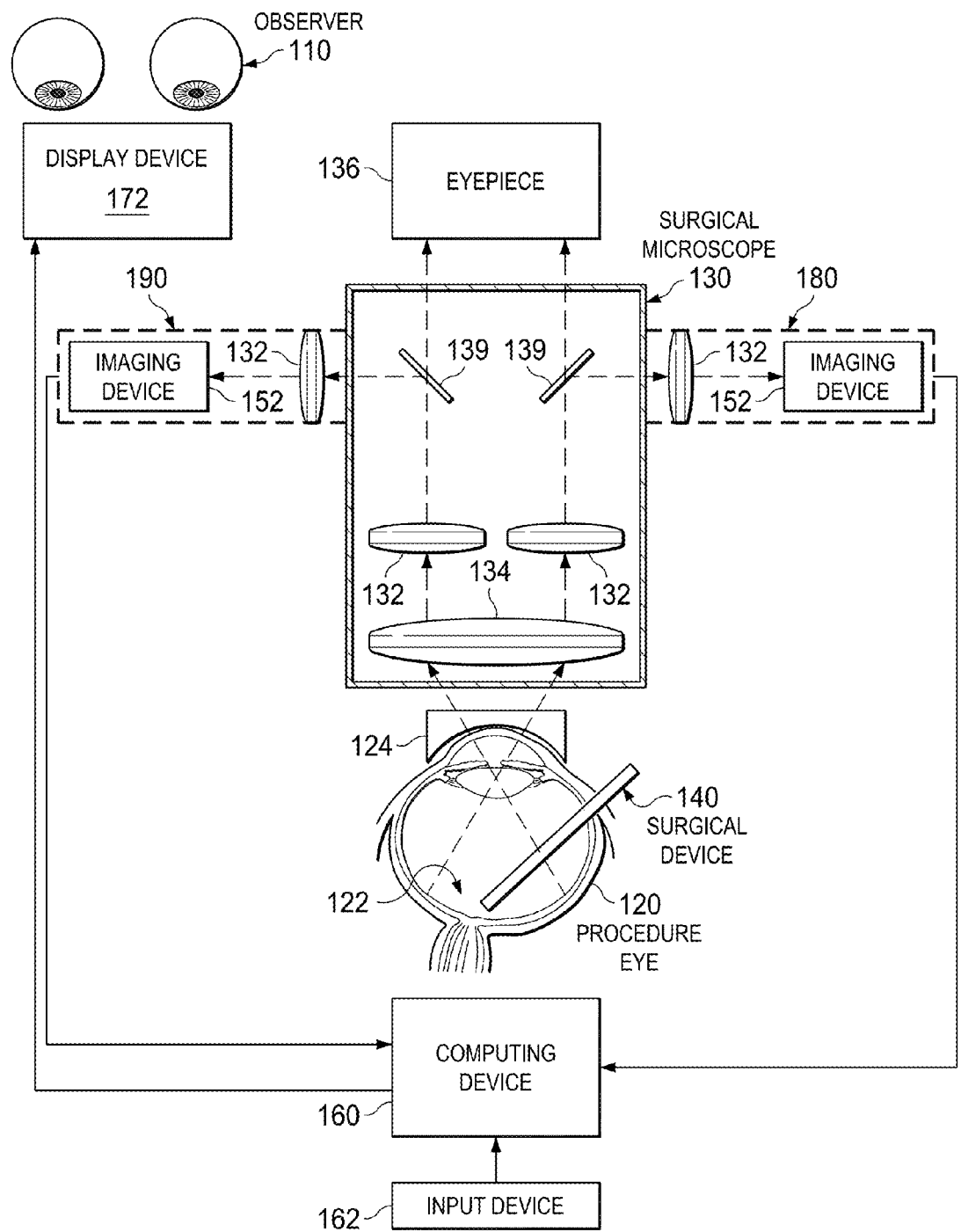

FIG. 13 is a schematic diagram of the ophthalmic visualization system 100 in which the surgical microscope 130 is a digital microscope. The observer 110 can observe the field of view of the surgical microscope 130 and/or and the graphical overlay 210 using the display device 172. In that regard, the display device 172 can be an external display device such that the observer 110 can view the surgical field 122 and/or the graphical overlay 210 on a screen or other suitable display area, in addition to and/or in lieu of looking through the eyepiece 136. The display device 172 can be two-dimensional (2D) display device configured to output two-dimensional images, such as a projection device and/or a monitor (e.g., flat screen or flat panel monitor). The display device 172 can be integrated with the surgical microscope 130 and/or a standalone component. The display device 172 can be a three-dimensional (3D) display device configured to output three-dimensional images and/or two-dimensional representations of three-dimensional objects. For example, a commercial 3D monitor, 3D television, etc., can be implemented as the display device 172. With a pair of 3D glasses, the observer 110 can see a stereoscopic view similar to that of an optical microscope. A 3D projector can be used to provide a cinema-like 3D view of the surgical field 122. In addition, a glasses-free 3D display based on holographic effect(s) can be implemented. The computing device 260 can provide a two-dimensional or three-dimensional display of the surgical field 122 and/or the graphical overlay 210 to a wearable device, such as an optical head-mounted display, smartglasses (e.g., Google Glass), etc. The computing device 160 receives data from the imaging device(s) 152, determines the area of interest, and then outputs a composite video stream to the 3D display/projector, in which both the original field of view and a magnified view of the area of interest are included. The eyepiece 136 can be removed from the surgical microscope 130. The 3D display/projector can be mounted to the surgical microscope 130 in front of the eye of the observer 110 to implement a heads-up display.

Figure 14:
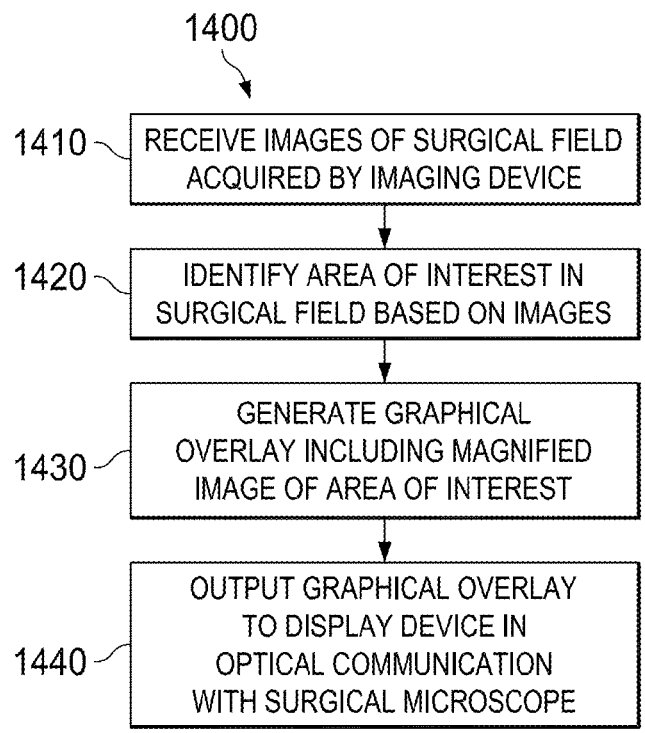
FIG. 14 is a flow diagram of a method of visualizing an ophthalmic procedure.

FIG. 14 is a flow diagram of a method 1400 of visualizing an ophthalmic procedure. The method 1400 can be better understood with reference to FIGS. 15-17. The method 1400 can include computer instructions executable by a processor, such as a processor of the computing device 160. As illustrated, the method 1400 includes a number of enumerated steps, but embodiments of the method 1400 may include additional steps before, after, and in between the enumerated steps. In some embodiments, one or more of the enumerated steps may be combined, omitted, or performed in a different order.

Figure 15:
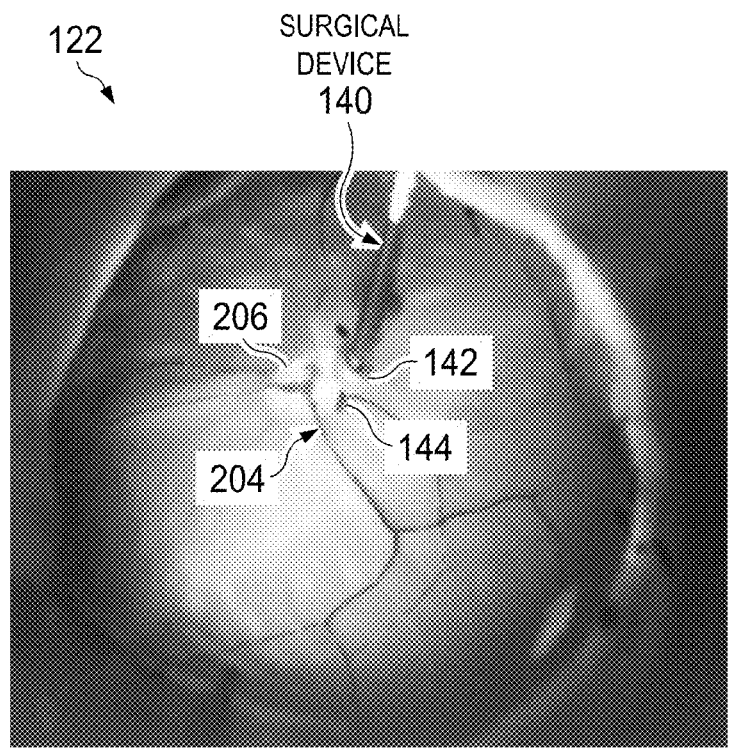
FIGS. 15, 16, and 17 are images of views of a surgical field using an ophthalmic visualization system.

The method 1400 can include, at step 1410, receiving images of the surgical field 122 acquired by the imaging device 152. An exemplary image of the surgical field 122, including the surgical device 140 and various anatomy such as the blood vessel 204 and the optic disk 206, is shown in FIG. 15. The method 1400 can include, at step 1420, identifying an area of interest in the surgical field 122 based on the images. For example, identifying the area of interest can include identifying, in the images, at least a portion of the surgical device 140 disposed in the surgical field 122. The at least a portion of the surgical device 140 can be identified in the images as the at least a portion of the surgical device 140 moves in the surgical field 122.

Figure 16:
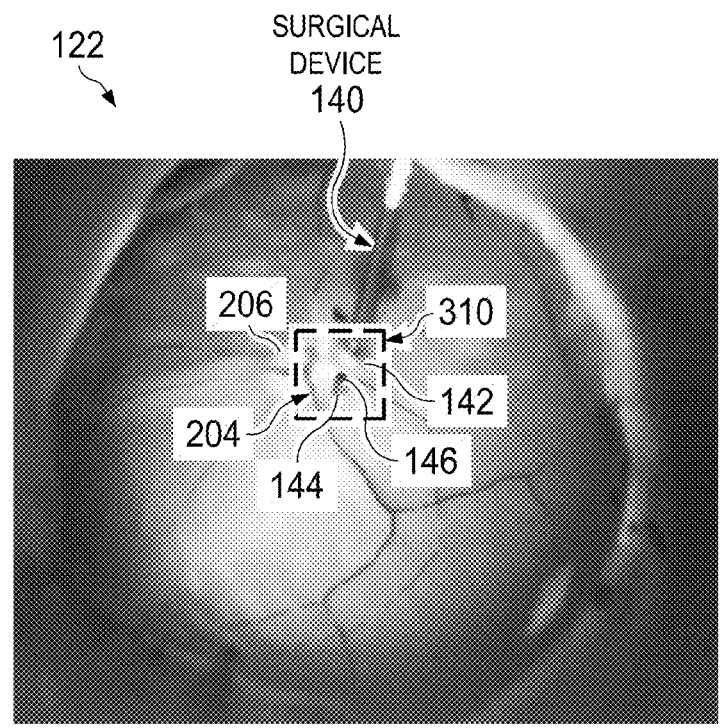

As shown in FIG. 16, the computing device 160 can identify the marker 142 and/or the tip 144 of the surgical device 140. The area of interest 310 can be an area around the marker 142 and/or the tip 144. The area can be defined by a size and shape around the marker 142 and/or the tip 144. The area of interest 310 can be various shapes including square, rectangle, polygon, circle, ellipse, other suitable shapes, and/or combinations thereof. The size of the area of interest 310 can be between about 1% and about 50%, between about 5% and about 40%, between about 10% and about 33%, between about 20% and about 25%, and/or other suitable proportions relative to the total field of view using the surgical microscope 130. The shape and/or size of the area of interest 310 can be set by the observer 110 using, e.g., the input device 162. Display data associated with the boundary of the area of interest 310 can be provided to the display device 172 such that the boundary is viewable using the surgical microscope 130. The boundary of the area of interest 310 can be representative of the processing steps carried out by the computing device 160 such that the outline is not viewable using the surgical microscope 130. The computing device 160 can generate display data associated with the indicator 146 provided to alert the observer 110 that the surgical device 140 is being tracked.

Figure 17:
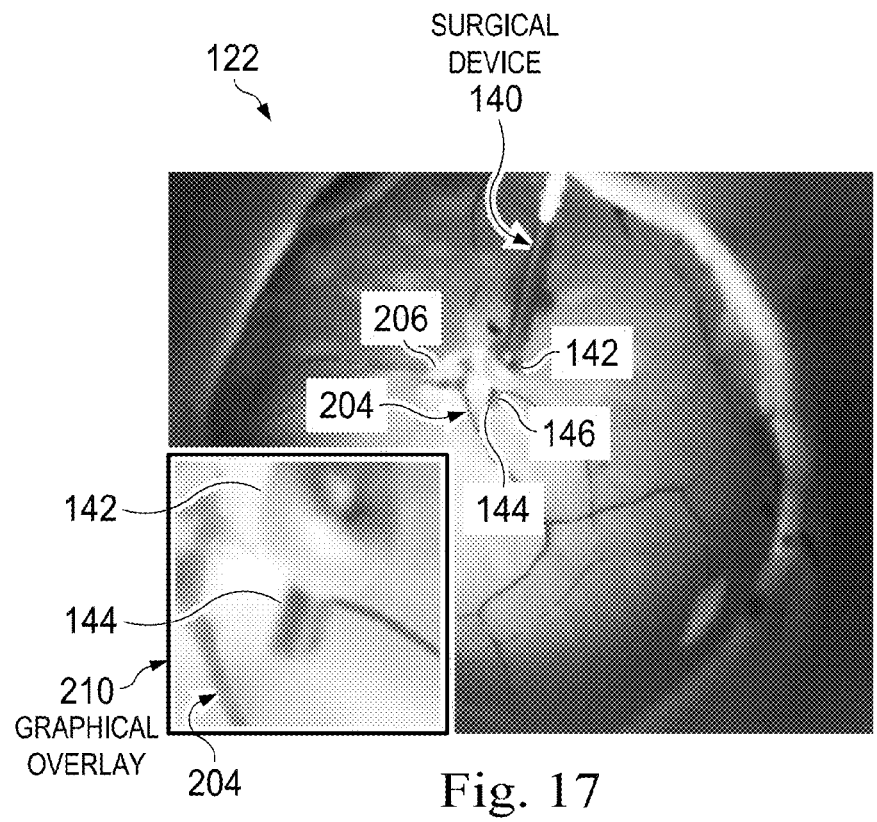

The method 1400 can include, at step 1430, generating a graphical overlay 210. The graphical overlay 210 can include a magnified image of the area of the interest. The method 1400 can include, at step 1440, outputting the graphical overlay 210 to the display device 172. The display device 172 can be in communication with the surgical microscope 130 configured to image the surgical field 122. The graphical overlay 210 can be viewable using the surgical microscope 130, as shown in FIG. 17. The graphical overlay 210 can be positioned over at least a portion of a field of view of the surgical microscope 130. The magnified image of the area of interest can be generated using image data from the same imaging device 152 used to identify the area of interest (step 1420) or a different imaging device 152.

For example, generating the graphical overlay 210 can include generating the graphical overlay 210 based on the images acquired by the imaging device 152, such as the imaging device 152 of the tracking and magnification module 150 (FIG. 1) or the imaging device 152 of the tracking module 180 (FIGS. 11 and 12).

The method 1400 can include receiving images of the surgical field 122 acquired by the imaging device 152, such as the imaging device 152 of the magnification module 190. Generating the graphical overlay 210 can include generating the graphical overlay 210 based on the images acquired by the imaging device 152 of the projection module 170. The method 1400 can include providing a control signal to move at least a portion of the imaging device 152, such as the imaging device 152 of the magnification module 190. The imaging device 152 of the magnification module 190 can be capable of acquiring images of the area of interest 310. The method 1400 can include receiving images of the area of interest 310 acquired by the imaging device 152 of the magnification module 190. Generating the graphical overlay 210 can include generating the graphical overlay 210 based on the images acquired by the imaging device 152 of the magnification module 190.

Outputting the graphical display 210 can include outputting the graphical overlay 210 in a fixed position when viewed using the surgical microscope 130. Outputting the graphical overlay 210 can include outputting the graphical overlay 210 in different positions when viewed using the surgical microscope. Outputting the graphical overlay includes outputting the graphical overlay 210 such that movement of graphical overlay 210 corresponds to movement of the at least a portion of the surgical device 140, such as the marker 142 and/or the tip 144. Outputting the graphical overlay 210 including outputting the graphical overlay 210 in a transparent manner such that the surgical field 122 is viewable through the graphical overlay 210 using the surgical microscope 130.

Embodiments as described herein can provide devices, systems, and methods that facilitate high magnification of an area of interest while simultaneously permitting a wide field of view during a surgical procedure. The examples provided above are exemplary only and are not intended to be limiting. One skilled in the art may readily devise other systems consistent with the disclosed embodiments which are intended to be within the scope of this disclosure. As such, the application is limited only by the following claims.

The invention claimed is:

1. An ophthalmic visualization system, comprising:
   a first imaging device configured to acquire first images of a surgical field;
   a computing device in communication with the first imaging device and configured to determine an area of interest in the surgical field based on the first images; and
   a first display device in communication with the computing device and a surgical microscope configured to image the surgical field, wherein the first display device is configured to provide a graphical overlay onto at least a portion of a field of view of the surgical microscope, and wherein the graphical overlay includes a magnified image of the area of interest.

2. The system of claim 1, wherein the computing device is configured to determine the area of interest by identifying, in the first images, at least a portion of a surgical device disposed in the surgical field.

3. The system of claim 1, wherein the first display device is configured to provide the graphical overlay such that the graphical overlay is viewable in a fixed position relative to the field of view of the surgical microscope.

4. The system of claim 1, wherein the first display device is configured to provide the graphical overlay such that the graphical overlay is viewable in variable positions relative to the field of view of the surgical microscope.

5. The system of claim 4, wherein:
the computing device is configured to identify at least a portion of a surgical device in the first images as the at least a portion of the surgical device moves in the surgical field; and
the first display device is configured to provide the graphical overlay such that movement of the graphical overlay corresponds to the movement of the at least a portion of the surgical device.

6. The system of claim 1, wherein the first display device is configured to provide the graphical overlay in a transparent manner such that the surgical field is viewable through the graphical overlay using the surgical microscope.

7. The system of claim 1, wherein the computing device is configured to generate the graphical overlay based on the first images.

8. The system of claim 1, further comprising:
a second imaging device in communication with the computing device and configured to acquire second images of the surgical field.

9. The system of claim 8, wherein the computing device is configured to generate the graphical overlay based on the second images.

10. The system of claim 1, further comprising:
a second imaging device in communication with the computing device, wherein the second imaging device includes optical zoom components and is configured to acquire images of the area of interest.

11. The system of claim 10, wherein the computing device is configured to:
determine the area of interest by identifying, in the first images, at least a portion of a surgical device disposed in the surgical field;
receive images of the area of interest acquired by the second imaging device; and
generate the graphical overlay based on the images of the area of interest.

12. The system of claim 10, wherein:
the computing device is configured to determine the area of interest in the first images by identifying at least a portion of a surgical device as the at least a portion of the surgical device moves in the surgical field; and
at least a portion of the second imaging device is movable such that the second imaging device is capable of acquiring the images of the area of interest as the at least a portion of the surgical device moves in the surgical field.

13. The system of claim 1, further comprising:
a second display device in communication with the computing device and the surgical microscope, wherein the surgical microscope comprises a stereo microscope, and wherein the first display device and second display device are associated with different optical paths of the stereo microscope.

14. The system of claim 1, wherein at least one of the first imaging device and the first display device is removably coupled to the surgical microscope.

15. The system of claim 1, wherein the surgical microscope comprises an optical microscope such that the field of view of the surgical microscope and the graphical overlay are observable through an eyepiece of the optical microscope.

16. The system of claim 1, wherein the surgical microscope comprises a digital microscope and the first display device comprises an external display device configured to output at least one of two-dimensional images and three-dimensional images, and wherein the field of view of the surgical microscope and the graphical overlay are observable using the external display device.

17. A method of visualizing an ophthalmic procedure, the method comprising:
receiving first images of a surgical field acquired by a first imaging device;
identifying an area of interest in the surgical field based on the first images;
generating a graphical overlay including a magnified image of the area of the interest; and
outputting the graphical overlay to a display device in communication with a surgical microscope configured to image the surgical field such that the graphical overlay is positioned over at least a portion of a field of view of the surgical microscope.

18. The method of claim 17, wherein identifying the area of interest includes identifying, in the first images, at least a portion of a surgical device disposed in the surgical field.

19. The method of claim 18, wherein outputting the graphical overlay includes outputting the graphical overlay in a fixed position relative to the field of view of the surgical microscope.

20. The method of claim 18, wherein outputting the graphical overlay includes outputting the graphical overlay in variable positions relative to the field of view of the surgical microscope.

21. The method of claim 20, wherein:
identifying the area of interest includes identifying, in the first images, at least a portion of a surgical device disposed in the surgical field as the at least a portion of the surgical device moves; and
outputting the graphical overlay includes outputting the graphical overlay such that movement of graphical overlay corresponds to the movement of the at least a portion of the surgical device.

22. The method of claim 17, wherein outputting the graphical overlay includes outputting the graphical overlay in a transparent manner such that the surgical field is viewable through the graphical overlay using the surgical microscope.

23. The method of claim 17, wherein generating a graphical overlay includes generating the graphical overlay using the first images.

24. The method of claim 17, further comprising receiving second images of the surgical field acquired by a second imaging device, and wherein generating a graphical overlay includes generating the graphical overlay using the second images.

25. The method of claim 17, further comprising:
providing a control signal to move at least a portion of a second imaging device such that the second imaging device is capable of acquiring images of the area of interest, wherein identifying the area of interest includes identifying, in the first images, at least a portion of a surgical device as the surgical devices moves in the surgical field; and receiving images of the area of interest acquired by the second imaging device, wherein generating a graphical overlay includes generating the graphical overlay using the second images.

* * * * *